United States Patent [19]

Braye

[11] 4,128,561
[45] Dec. 5, 1978

[54] PROCESS FOR THE PREPARATION OF 2-(2-THIENYL)-ETHYLAMINE AND DERIVATIVES THEREOF

[75] Inventor: Emile Braye, Auterive, France

[73] Assignee: Parcor, Paris, France

[21] Appl. No.: 749,033

[22] Filed: Dec. 8, 1976

Related U.S. Application Data

[62] Division of Ser. No. 640,142, Dec. 12, 1975, abandoned.

[51] Int. Cl.$^2$ .................. C07D 333/00; C07D 209/48; C07D 333/20
[52] U.S. Cl. ........................ 260/329 AM; 260/326 S
[58] Field of Search ...................... 260/326 S, 329 AM

[56] References Cited

U.S. PATENT DOCUMENTS 2,414,403  1/1947  Winterbottom .................. 260/326 S

OTHER PUBLICATIONS

Buehler and Pearson, "Organic Synthesis," (1970), p. 448.

Primary Examiner—A. Siegel

[57] ABSTRACT

This invention relates to a process for the preparation of compounds of the formula:

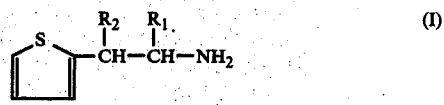

in which $R_1$ and $R_2$ may represent hydrogen or a lower alkyl or optionally substituted phenyl radical, comprising aminating a derivative of the formula:

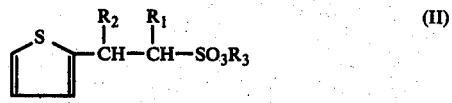

in which $R_3$ is an optionnally substituted alkyl, aryl or aralkyl group, and $R_1$ and $R_2$ are as defined for formula (I).

3 Claims, No Drawings

PROCESS FOR THE PREPARATION OF 2-(2-THIENYL)-ETHYLAMINE AND DERIVATIVES THEREOF

This is a division of application Ser. No. 640,142, filed Dec. 12, 1975, now abandoned.

This invention relates to a new process for the preparation of 2-(2-thienyl)-ethylamine and derivatives thereof, which are known compounds used as intermediates in the synthesis of a large number of derivatives used in both the chemical and pharmaceutical industries.

The compounds prepared according to the process of this invention have the following general formula:

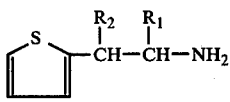
(I)

in which $R^1$ and $R^2$ each represent hydrogen or a lower alkyl or an optionally substituted phenyl radical. They have already been prepared according to a variety of methods. Thus, their synthesis was effected by reduction of 2-β-nitrovinyl-thiophene with lithium aluminum hydride (S. Gronovitz & Sandberg, Arkiv. for Kemi, 1970, 32, 217; M. L. Dressler, M. Soullie, J. Het. Chem., 1970, 7, 1257).

They have also been prepared from 2-(2-thienyl)-propylamide, by means of a Hoffman degradation reaction (G. Barger, A. Easson, J. Chem. Soc., 1938, 2100).

Other authors have also operated by reduction of 2-cyanomethyl thiophene with lithium aluminum hydride (B. F. Growe, F. F. Nord, J. Org. Chem., 1950, 15, 81; J. W. Mac Farland, H. L. Howes, J. Med. Chem., 1969, 12, 1079).

However, such prior methods are, all three, difficulty applicable industrially and do not provide compounds of the formula (I) in good yields.

Consequently, the object of the present invention is to provide an inexpensive industrial synthesis process which will produce 2-(2-thienyl)-ethylamine and derivatives thereof of the aforementioned formula (I) in good yields.

The process according to this invention comprises aminating a derivative of the formula:

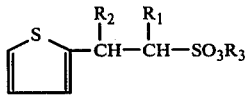
(II)

in which $R_1$ and $R_2$ are as defined for formula (I), and in which $R_3$ is an optionally substituted alkyl, aryl or aralkyl group, such as $CH_3$, $CCl_3$, $CF_3$, $p.CH_3\text{-}C_6H_4$, and the like.

According to en embodiment of the process of this invention, the amination is carried out directly by reacting the derivative of the formula (II) with ammonia.

The reaction is generally conducted in the hot, in an autoclave, during a period of time of 10-20 hours.

According to another embodiment of the process of this invention, the derivative of the formula (II) is reacted with phthalimide, to give a compound having the formula:

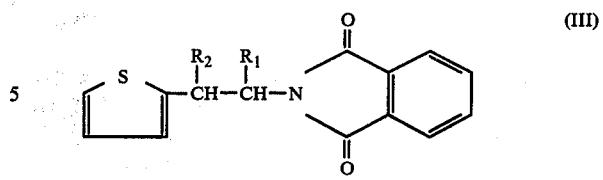

which is subsequently transaminated with an amine or hydrazine hydrate.

As amine, use is made of a markedly basic mono- or poly-functional amine of high boiling point. Typically useful amines have the formula $RNH_2$ in which R may be a $C_8\text{-}C_{25}$ straight or branched chain alkyl radical, an aralkyl radical (typically benzylamine and its substituted derivatives), an aryl radical such as an optionally substituted phenyl or naphthyl radical, particularly the halogeno-anilines, the alkyloxyanilines and benzidine. The radical R itself may carry other NH or $NH_2$ functions, as in bis(2-amino-ethyl)amine (diethylenetriamine), ethylenediamine, triethylenetetramine, or even other functional groups such as hydroxy, ester, alkoxy, and the like. Thus, the amine may be 4-hydroxy-butylamine, 2-pentoxy-propylamine, ethanolamine, and the like.

The reaction is preferably effected at elevated temperature, and diethylene triamine, benzylamine or ethanolamine are advantageously used.

The reaction of the derivative of the formula (II) with phthalimide is usually carried out in the presence of an inorganic or organic base, such as an alkali metal (Na, K) or alkaline-earth metal (Ca) carbonate or hydroxide, an alkali metal (Na, K) amide, an alkali metal (Na) hydride, an alkali metal alkoxide, and the like.

The following non limiting examples are given to illustrate the invention.

EXAMPLE 1

Preparation of 2-amino-1-(2-thienyl)propane, via direct amination

Into a 1000 ml autoclave, are added 1-(2-thienyl)-2-propanol p-toluenesulfonate (75 g) and ammonia (600 ml). The whole is heated to 80° C. during 15 hours. After cooling, the autoclave is opened and the ammonia is allowed to evaporate. After adding water (100 ml) and a 1N sodium hydroxide solution (175 ml), the resulting material is extracted with ether. The ether phase is separated and then mixed with 1N hydrochloric acid (75 ml). The aqueous phase is made alkaline and is then extracted with ether. The ether extract is washed with a 5% sodium bicarbonate solution, and then with a saturated sodium chloride solution, after which it is dried over sodium sulfate. After evaporation, the residue is distilled in vacuo, to give 19 g 2-amino-1-(2-thienyl)-propane (Yield: 53%) boiling at 84°–86° C. under 12 mm Hg.

EXAMPLE 2

Preparation of 2-(2-thienyl)-ethylamine, via indirect amination (a) Preparation of N-2-(2-thienyl)-ethyl phthalimide To a solution maintained at 80° C. and comprising 294g (2 moles) phthalimide dissolved in 800 ml dimethylformamide, are added 120 g anhydrous sodium carbonate followed, within 1.25 hour, by a solution of 564 g (2 moles) 2-(2-thienyl)-ethyl paratoluenesulfonate in 20 ml dimethylformamide. The reaction medium is maintained at 80° C. during 2 hours and 20 minutes and is then cooled and poured over 1 liter water.

The resulting precipitate is collected by filtration; it is then washed, dried and recrystallized from ethanol, to give 396 g N-2-(2-thienyl)-ethylphthalimide (Yield: 44%) which has a melting point (Koefler block) of 129°–130° C.

(b) Preparation of 2-(2-thienyl)-ethylamine 51.4 g (0.2 mole) of the N-2-(2-thienyl)-ethyl phthalimide are mixed with 10.3 g diethylenetriamine (0.1 mole) and heated at 120° C. during 4 hours. The pressure is then gradually decreased to 19 Torr, and distillation gives 19.7 g 2-(2-thienyl)-ethylamine (Yield: 77%) which has a boiling point of 98° C./19 Torr.

Having now described my invention what I claim as new and desire to secure by Letters Patent is:

1. Process for the preparation of compounds having the formula:

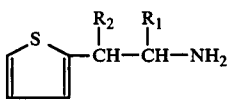

in which $R_1$ and $R_2$ are each selected from the group consisting of hydrogen, the lower alkyl groups, the phenyl radical and the substituted phenyl radicals, comprising reacting in the presence of a base a derivative of the formula:

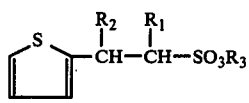

in which $R_1$ and $R_2$ have the above-defined meanings and $R_3$ is selected from the alkyl, substituted alkyl, aryl, substituted aryl, aralkyl and substituted aralkyl groups with phthalimide, to give a compound having the formula:

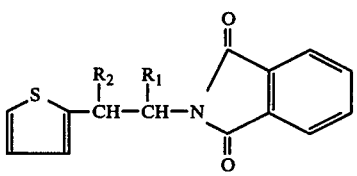

which is subsequently transaminated by reacting with an amine at elevated temperature.

2. Process as claimed in claim 1, wherein the amine is selected from the group consisting of diethylenetriamine, benzylamine and ethanolamine.

3. A process as claimed in claim 1, in which the first-mentioned reaction is conducted at a temperature of about 80° C.

* * * * *